(12) United States Patent
Hogg et al.

(10) Patent No.: US 9,340,573 B2
(45) Date of Patent: May 17, 2016

(54) AZAINDOLINES

(71) Applicant: Hoffmann-La Roche Inc., Nutley, NJ (US)

(72) Inventors: Joan Heather Hogg, Caldwell, NJ (US); Yan Lou, Pleasanton, CA (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/433,251

(22) PCT Filed: Oct. 8, 2013

(86) PCT No.: PCT/EP2013/070877
§ 371 (c)(1),
(2) Date: Apr. 2, 2015

(87) PCT Pub. No.: WO2014/056867
PCT Pub. Date: Apr. 17, 2014

(65) Prior Publication Data
US 2015/0252072 A1    Sep. 10, 2015

Related U.S. Application Data

(60) Provisional application No. 61/712,330, filed on Oct. 11, 2012.

(51) Int. Cl.
| | | |
|---|---|---|
| *C07D 401/02* | (2006.01) | |
| *C07D 401/10* | (2006.01) | |
| *A61K 31/437* | (2006.01) | |
| *A61K 31/4353* | (2006.01) | |
| *C07K 5/062* | (2006.01) | |
| *C07D 471/04* | (2006.01) | |

(52) U.S. Cl.
CPC .......... *C07K 5/06026* (2013.01); *C07D 471/04* (2013.01)

(58) Field of Classification Search
CPC .................. A61K 31/437; A61K 31/4353
USPC ............................................ 546/113; 514/300
See application file for complete search history.

(56) References Cited

FOREIGN PATENT DOCUMENTS

| WO | 2006017295 | 2/2006 |
|---|---|---|
| WO | 2010017035 | 2/2010 |

OTHER PUBLICATIONS

The International Search Report and Written Opinion, mailed on Nov. 12, 2013, in the corresponding PCT Appl. No. PCT/EP2013/070877.

*Primary Examiner* — Niloofar Rahmani

(57) ABSTRACT

Disclosed are compounds of Formula (I) or pharmaceutically acceptable salts thereof, wherein W, Y, Z, $R^1$, $R^2$, $R^3$ and $R^4$ are as described in this application, and methods of using the compounds in the treatment of cancer.

(I)

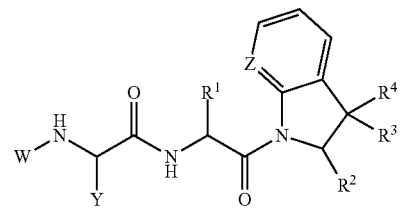

33 Claims, No Drawings

```
                        SEQUENCE LISTING

<160> NUMBER OF SEQ ID NOS: 3

<210> SEQ ID NO 1
<211> LENGTH: 10
<212> TYPE: PRT
<213> ORGANISM: Artificial Sequence
<220> FEATURE:
<223> OTHER INFORMATION: TR-FRET peptide

<400> SEQUENCE: 1

Ala Val Pro Ile Ala Gln Lys Ser Glu Lys
1               5                   10

<210> SEQ ID NO 2
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 2

Met Arg His His His His His His Arg Asp His Phe Ala Leu Asp Arg
1               5                   10                  15

Pro Ser Glu Thr His Ala Asp Tyr Leu Leu Arg Thr Gly Gln Val Val
            20                  25                  30

Asp Ile Ser Asp Thr Ile Tyr Pro Arg Asn Pro Ala Met Tyr Ser Glu
        35                  40                  45

Glu Ala Arg Leu Lys Ser Phe Gln Asn Trp Pro Asp Tyr Ala His Leu
    50                  55                  60

Thr Pro Arg Glu Leu Ala Ser Ala Gly Leu Tyr Tyr Thr Gly Ile Gly
65                  70                  75                  80

Asp Gln Val Gln Cys Phe Ala Cys Gly Gly Lys Leu Lys Asn Trp Glu
                85                  90                  95

Pro Gly Asp Arg Ala Trp Ser Glu His Arg Arg His Phe Pro Asn Cys
            100                 105                 110

Phe Phe Val Leu Gly Arg Asn Leu Asn Ile Arg Ser Glu
```

```
<210> SEQ ID NO 3
<211> LENGTH: 125
<212> TYPE: PRT
<213> ORGANISM: Artificial Sequence
<220> FEATURE:
<223> OTHER INFORMATION: TR-FRET peptide

<400> SEQUENCE: 3

Met Arg His His His His His Arg Ser Asp Ala Val Ser Ser Asp
1               5                   10                  15

Arg Asn Phe Pro Asn Ser Thr Asn Leu Pro Arg Asn Pro Ser Met Ala
            20                  25                  30

Asp Tyr Glu Ala Arg Ile Phe Thr Phe Gly Thr Trp Ile Tyr Ser Val
        35                  40                  45

Asn Lys Glu Gln Leu Ala Arg Ala Gly Phe Tyr Ala Leu Gly Glu Gly
    50                  55                  60

Asp Lys Val Lys Cys Phe His Cys Gly Gly Gly Leu Thr Asp Trp Lys
65                  70                  75                  80

Pro Ser Glu Asp Pro Trp Glu Gln His Ala Lys Trp Tyr Pro Gly Cys
                85                  90                  95

Lys Tyr Leu Leu Glu Gln Lys Gly Gln Glu Tyr Ile Asn Asn Ile His
            100                 105                 110

Leu Thr His Ser Leu Glu Glu Cys Leu Val Arg Thr Thr
            115                 120                 125
```

AZAINDOLINES

CROSS-REFERENCE TO RELATED APPLICATIONS

This application is a National Stage Application of PCT/EP2013/070877 filed Oct. 8, 2013, which claims priority from U.S. Provisional Patent Application No. 61/712,330, filed on Oct. 11, 2012. The priority of both said PCT and U.S. Provisional Patent Application are claimed. Each of the prior mentioned applications is hereby incorporated by reference herein in its entirety.

FIELD OF THE INVENTION

The present invention relates to azaindolines which act as inhibitors of SMAC protein binding to Inhibitor of Apoptosis Proteins (IAPs), and/or inhibitors of activated caspase protein binding to IAPs. These molecules are useful in the amelioration, treatment or control of cancer, especially solid tumors.

These compounds bind to the BIR2 and/or BIR3 regions of IAP proteins, including XIAP and cIAP, resulting in activation or reactivation of the caspase cascade and, as such, are useful for the treatment of proliferative diseases, including cancer.

BACKGROUND OF THE INVENTION

Cancer is a disease of uncontrolled cell growth causing local expansion of a tumor and, potentially, distant metastases. One mechanism by which cancer cells grow is by avoidance of apoptosis, or programmed cell death. Alterations in apoptotic pathways have been linked to cancer cells being resistant to standard treatments, e.g., chemotherapeutics or radiation, and to the incidence and progression of cancer. See, e.g., E. Dean et al., "X-linked inhibitor of apoptosis protein as a therapeutic target," Expert Opin. Ther. Targets (2007) 11(11):1459-1471

The two basic pathways for apoptotic cell death are the intrinsic pathway and the extrinsic pathway. The intrinsic apoptotic pathway can be initiated by various mechanisms including cellular stress and drug-induced DNA damage. The extrinsic pathway can be initiated by activation of the death receptors by a chemokine. Initiation of either pathway results in the activation of a family of proteases called caspases. Once activated, the caspases can act to cleave a variety of substrates creating a cascade of events that lead to the activation of the effector caspases 3 and 7 and eventual cell death. The IAP family of proteins can bind to and inhibit the activity of caspases thus inhibiting apoptosis. See, e.g., Dean, supra at 1460.

The IAPs can contain up to three copies of homologous structural domains called baculoviral IAP repeat (BIR) domains, BIR1, BIR2 and BIR3. The BIR3 domain of the prototypical IAPs, cIAP and XIAP, can bind to and inhibit activated caspase 9. The BIR2 domain, in contrast, binds to and inhibits caspases 3 and 7. The proapoptotic protein Smac (also known as DIABLO) can block the BIR2 and BIR3 domains of IAPs competing with activated caspases resulting in release of the activated caspases from the IAPs and completion of the apoptotic program. See, e.g., S. Wang, "Design of Small-Molecule Smac Mimetics as IAP Antagonists," Current Topics in Microbiology and Immunology 348, DOI 10.1007/82_2010_111, pp. 89-113.

Peptides and small molecules have been reported to bind to the BIR3 region of XIAP and cIAP, mimicking the action of Smac protein and releasing activated caspases. See, e.g., Dean, supra; and M. Gyrd-Hanse et al., "IAPs: From caspase inhibitors to modulators of NF-κB, inflammation and cancer," Nature Review/Cancer, August 2010, Vol 10:561-574.

SUMMARY OF THE INVENTION

One aspect of the present invention is a compound of Formula I

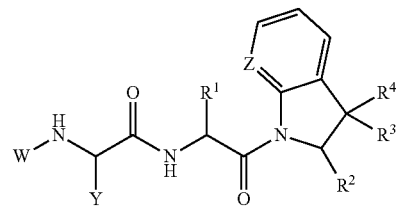

or pharmaceutically acceptable salts thereof, wherein W, Y, Z, $R^1$, $R^2$, $R^3$ and $R^4$ are as described in this application.

The present invention also relates to pharmaceutical compositions comprising one or more compounds of the invention, or a pharmaceutically acceptable salt thereof, and a pharmaceutically acceptable carrier or excipient.

The present invention further relates to a method of ameliorating, controlling or treating cancer, including specifically solid tumors, for example lung, pancreatic, colon, breast, bone and prostate cancers in a mammal, specifically a human, comprising administering to said mammal a therapeutically effective amount of a compound according to the invention or a pharmaceutically acceptable salt thereof.

DETAILED DESCRIPTION OF THE INVENTION

Definitions

Unless otherwise defined, all technical and scientific terms used herein have the same meaning as commonly understood by one of ordinary skill in the art to which this invention belongs.

As used herein, the following terms shall have the following definitions.

"Alkyl" means a monovalent linear or branched saturated hydrocarbon of 1 to 12 carbon atoms. In particular embodiments, alkyl has 1 to 6 carbon atoms, and in more particular embodiments 1 to 4 carbon atoms. As used herein, "lower alkyl" denotes an alkyl group having from 1-6 carbon atoms ("$C_{1-6}$-alkyl"). Examples of alkyl include methyl, ethyl, propyl, isopropyl, butyl (also known as n-butyl), iso-butyl, sec-butyl, tert-butyl, pentyl, hexyl, and the like. The alkyl group can be optionally enriched in deuterium, e.g., —$CD_3$, —$CD_2CD_3$ and the like.

"Aryl" means a monovalent aromatic carbocyclic mono-, bi- or tricyclic ring system comprising 6 to 19 carbon ring atoms. Examples of aryl moieties include, but are not limited to, phenyl, naphthyl (also known as naphthalenyl), tolyl, xylyl, pyridinyl, quinolinyl, pyrimidinyl, imidazolyl, thiazolyl, anthracenyl, tetrazolyl, and fluorenyl.

"Benzyl" means —$CH_2$-phenyl.

"Cyano" means —C≡n.

"Cycloalkyl" means a substituted on unsubstituted stable monovalent saturated monocyclic, bicyclic or tricyclic system which consists of 3 to 10 ring carbon atoms. In particular embodiments cycloalkyl denotes a monovalent saturated monocyclic hydrocarbon group of 3 to 8 ring carbon atoms, in particular monovalent saturated monocyclic hydrocarbon group of 3 to 7 ring carbon atoms ("$C_{3-7}$-cycloalkyl"). Particular cycloalkyl groups are monocyclic. Examples for monocyclic cycloalkyl are cyclopropyl, cyclobutnyl, cyclopentyl, cyclohexyl or cycloheptyl. Bicyclic means consisting of two saturated carbocycles having one or more carbon atoms in common. Examples for bicyclic cycloalkyl are bicyclo[2.2.1]heptanyl, or bicyclo[2.2.2]octanyl. Tricyclic means consisting of three saturated carbocycles having two or more carbon atoms in common. Examples of tricyclic cycloalkyl include adamantane.

"Halogen" or "Halo" means at atom selected from F, Cl, Br or I. In particular embodiments Halogen means F and Cl.

"Heteroatom" means at atom selected from N, O or S.

"Heteroaryl" means a substituted or unsubstituted aromatic heterocyclic ring system containing up to two rings, at least one ring of which includes 1, 2, or 3 heteroatoms, the remaining ring atoms being carbon. Examples of heteroaryl groups include, but are not limited to, thienyl (also known as thiophenyl), furyl (also known as furanyl), indolyl, pyrrolyl, pyridinyl, pyrazinyl, oxazolyl, isoxazolyl, oxadiazolyl, thiazolyl, quinolinyl, isoquinolinyl, indazolyl, pyrimidinyl, imidazolyl, triazolyl, tetrazolyl, triazinyl, pyrazolyl, benzo[d]isoxazolyl, 2-oxo-2H-chromen-4-yl, benzo[d]isoxazolyl, benzothiophenyl, benzoimidazolyl, naphthyridinyl and cinnolinyl.

In the case of a heteroaryl that is bicyclic it should be understood that one ring may be aryl while the other is heteroaryl and both may be independently substituted or unsubstituted.

"Heterocyclyl," "heterocycle" or "heterocyclic ring" means a substituted or unsubstituted monovalent saturated or partly unsaturated mono- or bicyclic ring, non-aromatic hydrocarbon system of 3 to 9 ring atoms, comprising 1, 2, or 3 ring heteroatoms selected from N, O and S, the remaining ring atoms being carbon. In particular embodiments, heterocycloalkyl is a monovalent saturated monocyclic ring system of 4 to 7 ring atoms, comprising 1, 2, or 3 ring heteroatoms selected from N, O and S, the remaining ring atoms being carbon. Examples for monocyclic saturated heterocycloalkyl are aziridinyl, oxiranyl, azetidinyl, oxetanyl, pyrrolidinyl, tetrahydrofuranyl, tetrahydro-thienyl, pyrazolidinyl, imidazolidinyl, oxazolidinyl, isoxazolidinyl, thiazolidinyl, piperidinyl, tetrahydropyranyl, tetrahydrothiopyranyl, tetrahydrofuranyl, piperazinyl, morpholinyl, thiomorpholinyl, 1,1-dioxo-thiomorpholin-4-yl, azepanyl, diazepanyl, homopiperazinyl, or oxazepanyl. Examples of partly unsaturated heterocycloalkyl are dihydrofuryl, imidazolinyl, dihydro-oxazolyl, dihydro-oxadiazolyl, dihydro-triazolyl, tetrahydro-pyridinyl, tetrahydro-triazinyl or dihydropyranyl.

In the case of a heterocycle that is bicyclic it should be understood that one ring may be heterocycle while the other is cycloalkyl, and either or both may be independently substituted. Examples for bicyclic saturated heterocycloalkyl are 8-aza-bicyclo[3.2.1]octyl, quinuclidinyl, 8-oxa-3-aza-bicyclo[3.2.1]octyl, 9-aza-bicyclo[3.3.1]nonyl, 3-oxa-9-aza-bicyclo[3.3.1]nonyl, or 3-thia-9-aza-bicyclo[3.3.1]nonyl.

"$IC_{50}$" refers to the concentration of a particular compound required to inhibit 50% of a specific measured activity. $IC_{50}$ can be measured, inter alia, as is described subsequently in Example 15.

"Pharmaceutically acceptable," such as pharmaceutically acceptable carrier, excipient, etc., means pharmacologically acceptable and substantially non-toxic to the subject to which the particular compound is administered.

"Pharmaceutically acceptable salt" refers to conventional acid-addition salts or base-addition salts that retain the biological effectiveness and properties of the compounds of the present invention and are formed from suitable non-toxic organic or inorganic acids or organic or inorganic bases. Sample acid-addition salts include those derived from inorganic acids such as hydrochloric acid, hydrobromic acid, hydroiodic acid, sulfuric acid, sulfamic acid, phosphoric acid and nitric acid, and those derived from organic acids such as p-toluenesulfonic acid, salicylic acid, methanesulfonic acid, oxalic acid, succinic acid, citric acid, malic acid, lactic acid, fumaric acid, trifluoroacetic acid and the like. Sample base-addition salts include those derived from ammonium, potassium, sodium and, quaternary ammonium hydroxides, such as for example, tetramethylammonium hydroxide. Chemical modification of a pharmaceutical compound (i.e. drug) into a salt is a technique well known to pharmaceutical chemists to obtain improved physical and chemical stability, hygroscopicity, flowability and solubility of compounds. See, e.g., Ansel et al., Pharmaceutical Dosage Forms and Drug Delivery Systems (1995) at pgs. 456-457.

"Substituted," as in substituted alkyl, aryl or heteroaryl means that the substitution (i.e. replacement of one hydrogen atom) can occur at one or more positions and, unless otherwise indicated, that the substituents at each substitution site are independently selected from the specified options. The term "optionally substituted" refers to the fact that one or more hydrogen atoms of a chemical group (with one or more hydrogen atoms) can be, but does not necessarily have to be, substituted with another substituent.

As used in this application, if a formula or group appears to be missing a substituent, that is it appears the valence is not complete, it is presumed the missing substituent is an H.

In the structural formulae presented herein a broken bond (a) denotes that the substituent is below the plane of the paper and a wedged bond (b) denotes that the substituent is above the plane of the paper.

In one embodiment, the present invention relates to compounds of Formula I

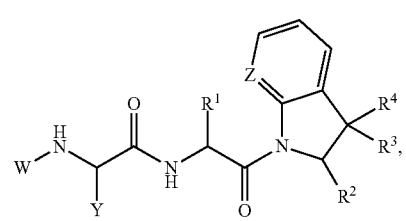

I wherein
W is selected from the group
a) H,
b) alkyl that optionally includes 1-3 deuterium atoms,
c) alkyl that optionally may be substituted with $SO_2R^5$ and $OR^5$ Y is alkyl that optionally may be substituted with $OR^5$;
Z is N;
$R^1$ is selected from the group
a) lower alkyl that optionally may be substituted with $SO_2R^5$,
b) cycloalkyl,
c) heterocyclic, and
d) aryl;
$R^2$ is lower alkyl that optionally may be substituted with $NHC(O)R^6$, $NHSO_2R^5$, $NHCOOR^6$ and $NHR^6$;

R³ and R⁴ may be the same or different and each is independently selected from the group
a) H, and
b) lower alkyl;
R⁵ is selected from the group
a) H,
b) lower alkyl,
c) NR⁷R⁸, and
d) aryl;
R⁶ is selected from the group
a) H
b) aryl that optionally may be substituted with lower alkyl, OR⁵, halogen, C(O)OR⁵, C(O)NR⁷R⁸, aryl, heterocyclyl, C(O)R⁹, SO₂R⁵, cyano and CF₃,
c) lower alkyl that optionally may be substituted with CF₃, SO₂R⁵ and aryl that optionally may be substituted with lower alkyl and halogen,
d) OR⁵,
e) NR⁷R⁸,
f) heteroaryl that optionally may be substituted with lower alkyl, OR⁵, halogen, aryl and oxo, and
g) heterocyclyl;
R⁷ and R⁸ may be the same or different and each is independently selected from the group
a) H,
b) lower alkyl, and
c) aryl; and
R⁹ is selected from the group
a) lower alkyl, and
b) aryl;
or a pharmaceutically acceptable salt thereof.

One embodiment of the invention relates to compounds of Formula I wherein W is selected from the group
a) H,
b) $C_{1-6}$-alkyl that optionally includes 1-3 deuterium atoms,
c) $C_{1-6}$-alkyl that optionally may be substituted with SO₂R⁵ and OR⁵
Y is $C_{1-6}$-alkyl that optionally may be substituted with OR⁵;
Z is N;
R¹ is selected from the group
a) $C_{1-6}$-alkyl that optionally may be substituted with SO₂R⁵,
b) $C_{3-7}$-cycloalkyl,
c) heterocyclic, and
d) aryl;
R² is $C_{1-6}$-alkyl that optionally may be substituted with NHC(O)R⁶, NHSO₂R⁵, NHCOOR⁶ and NHR⁶;
R³ and R⁴ may be the same or different and each is independently selected from the group
a) H, and
b) $C_{1-6}$-alkyl;
R⁵ is selected from the group
a) H,
b) $C_{1-6}$-alkyl,
c) NR⁷R⁸, and
d) aryl;
R⁶ is selected from the group
a) H
b) aryl that optionally may be substituted with $C_{1-6}$-alkyl, OR⁵, halogen, C(O)OR⁵, C(O)NR⁷R⁸, aryl, heterocyclyl, C(O)R⁹, SO₂R⁵, cyano and CF₃,
c) $C_{1-6}$-alkyl that optionally may be substituted with CF₃, SO₂R⁵ and aryl that optionally may be substituted with $C_{1-6}$-alkyl and halogen,
d) OR⁵,
e) NR⁷R⁸,
f) heteroaryl that optionally may be substituted with $C_{1-6}$-alkyl, OR⁵, halogen, aryl and oxo, and
g) heterocyclyl;
R⁷ and R⁸ may be the same or different and each is independently selected from the group
a) H,
b) $C_{1-6}$-alkyl, and
c) aryl; and
R⁹ is selected from the group
a) $C_{1-6}$-alkyl, and
b) aryl;
or a pharmaceutically acceptable salt thereof.

One embodiment of the invention relates to compounds of Formula I wherein
W is $C_{1-6}$-alkyl;
Y is $C_{1-6}$-alkyl;
Z is N;
R¹ is $C_{1-6}$-alkyl;
R² is $C_{1-6}$-alkyl that optionally may be substituted with NHC(O)R⁶, NHSO₂R⁵, NHCOOR⁶ and NHR⁶;
R³ and R⁴ are both H; R⁵ is selected from the group
a) $C_{1-6}$-alkyl, and
b) aryl;
R⁶ is selected from the group
a) aryl,
b) $C_{1-6}$-alkyl that optionally may be substituted with aryl, and
c) NR⁷R⁸,
R⁷ and R⁸ may be the same or different and each is independently selected from the group
a) H,
b) $C_{1-6}$-alkyl, and
c) aryl;
or a pharmaceutically acceptable salt thereof.

One embodiment of the invention relates to compounds of Formula I wherein
W is $C_{1-6}$-alkyl;
Y is $C_{1-6}$-alkyl;
Z is N;
R¹ is $C_{1-6}$-alkyl;
R² is $C_{1-6}$-alkyl that optionally may be substituted with NHC(O)R⁶, NHSO₂R⁵, NHCOOR⁶ and NHR⁶;
R³ and R⁴ are both H;
R⁵ is selected from the group
a) methyl, and
b) phenyl
R⁶ is selected from the group
a) phenyl,
b) benzyl,
c) —C(H,CH₃)-phenyl,
d) naphthyl,
e) methyl,
f) NH₂,
g) N(methyl)₂,
h) N(H,methyl); and
i) N(H,phenyl);
or a pharmaceutically acceptable salt thereof.

One embodiment of the invention relates to compounds of Formula I wherein
W is $C_{1-6}$-alkyl;
Y is $C_{1-6}$-alkyl;
Z is N;
R¹ is $C_{1-6}$-alkyl;
R² is —CH₂—NHC(O)R⁶, $R^3$ and $R^4$ are both H;
$R^6$ is selected from the group
a) phenyl,
b) benzyl,
c) —C(H,CH$_3$)-phenyl,
d) naphthyl,
e) methyl,
f) NH$_2$,
g) N(methyl)$_2$,
h) N(H,methyl); and
i) N(H,phenyl);
or a pharmaceutically acceptable salt thereof.

One embodiment of the invention relates to compounds of Formula I wherein
W is $C_{1-6}$-alkyl;
Y is $C_{1-6}$-alkyl;
Z is N;
$R^1$ is $C_{1-6}$-alkyl;
$R^2$ is —CH$_2$—NHC(O)R$^6$,
$R^3$ and $R^4$ are both H;
$R^6$ is selected from the group
a) phenyl,
b) —C(H,CH$_3$)-phenyl,
c) methyl,
d) N(methyl)$_2$,
e) N(H,methyl); and
f) N(H,phenyl);
or a pharmaceutically acceptable salt thereof.

One embodiment of the invention relates to compounds of Formula I wherein W is $C_{1-6}$-alkyl.

One embodiment of the invention relates to compounds of Formula I wherein W is methyl.

One embodiment of the invention relates to compounds of Formula I wherein Y is $C_{1-6}$-alkyl.

One embodiment of the invention relates to compounds of Formula I wherein Y is methyl.

One embodiment of the invention relates to compounds of Formula I wherein $R^1$ is $C_{1-6}$-alkyl, or a pharmaceutically acceptable salt thereof.

One embodiment of the invention relates to compounds of Formula I wherein $R^1$ is propanyl.

One embodiment of the invention relates to compounds of Formula I wherein $R^2$ is $C_{1-6}$-alkyl that is substituted with NHC(O)R$^6$, or a pharmaceutically acceptable salt thereof.

One embodiment of the invention relates to compounds of Formula I wherein $R^2$ is methyl that is substituted with NHC(O)R$^6$ and $R^6$ is selected from aryl and $C_{1-6}$-alkyl, or a pharmaceutically acceptable salty thereof.

One embodiment of the invention relates to compounds of Formula I wherein $R^2$ is $C_{1-6}$-alkyl that is substituted with NHSO$_2$R$^5$, or a pharmaceutically acceptable salt thereof.

One embodiment of the invention relates to compounds of Formula I wherein $R^2$ is methyl that is substituted with NHSO$_2$R$^5$.

One embodiment of the invention relates to compounds of Formula I wherein $R^5$ is methyl or phenyl.

One embodiment of the invention relates to compounds of Formula I wherein $R^2$ is $C_{1-6}$-alkyl that is substituted with NHCOOR$^6$, or a pharmaceutically acceptable salt thereof.

One embodiment of the invention relates to compounds of Formula I wherein $R^6$ is benzyl or methyl that optionally may be substituted with phenyl, or a pharmaceutically acceptable salt thereof.

One embodiment of the invention relates to compounds of Formula I wherein $R^2$ is $C_{1-6}$-alkyl that is substituted with NHR$^6$, or a pharmaceutically acceptable salt thereof.

One embodiment of the invention relates to compounds of Formula I wherein $R^6$ is aryl, or a pharmaceutically acceptable salt thereof.

One embodiment of the invention relates to compounds of Formula I wherein $R^6$ is phenyl or naphathanelyl, or a pharmaceutically acceptable salt thereof.

One embodiment of the invention relates to compounds of Formula I wherein $R^3$ and $R^4$ are H, or a pharmaceutically acceptable salt thereof.

One embodiment of the invention relates to compounds of Formula I wherein $R^6$ is phenyl that optionally may be substituted with $C_{1-6}$-alkyl, OR$^5$, halogen, C(O)OR$^5$, C(O)NR$^7$R$^8$, aryl, heterocyclyl, C(O)R$^9$, SO$_2$R$^5$, cyano and CF$_3$, or a pharmaceutically acceptable salt thereof.

One embodiment of the invention relates to compounds of Formula I wherein wherein $R^6$ is NR$^7$R$^8$, or a pharmaceutically acceptable salt thereof.

One embodiment of the invention relates to compounds of Formula I wherein $R^7$ and $R^8$ are independently selected from H, methyl and phenyl.

One embodiment of the invention relates to compounds of Formula I wherein W, Y and $R^1$ are $C_{1-6}$-alkyl; and $R^2$ is $C_{1-6}$-alkyl substituted by NHCOR$^6$; $R^6$ is selected from a) phenyl, b) $C_{1-6}$-alkyl that optionally may be substituted with phenyl, and c) NR$^7$R$^8$; and $R^7$ and $R^8$ are each independently selected from H, $C_{1-6}$-alkyl and phenyl; or a pharmaceutically acceptable salt thereof.

One embodiment of the invention relates to compounds of Formula I wherein W, Y and $R^1$ are $C_{1-6}$-alkyl; $R^2$ is $C_{1-6}$-alkyl substituted by NHSO$_2$R$^5$; and $R^5$ is $C_{1-6}$-alkyl or phenyl; or a pharmaceutically acceptable salt thereof.

One embodiment of the invention relates to compounds of Formula I wherein $R^5$ is methyl or phenyl.

One embodiment of the invention relates to compounds of Formula I wherein W, Y and $R^1$ are $C_{1-6}$-alkyl; $R^2$ is $C_{1-6}$-alkyl substituted by NHCOOR$^6$; and $R^6$ is selected from a) aryl and b) $C_{1-6}$-alkyl that optionally may be substituted with aryl; or a pharmaceutically acceptable salt thereof.

One embodiment of the invention relates to compounds of Formula I wherein $R^6$ is selected from a) methyl that optionally may be substituted with phenyl, and b) phenyl; or a pharmaceutically acceptable salt thereof.

One embodiment of the invention relates to compounds of Formula I wherein W, Y and $R^1$ are $C_{1-6}$-alkyl; $R^2$ is $C_{1-6}$-alkyl substituted by NHR$^6$; and $R^6$ is aryl, or a pharmaceutically acceptable salt thereof.

One embodiment of the invention relates to compounds of Formula I wherein $R^6$ is selected from phenyl and naphthalenyl.

One embodiment of the invention relates to compounds of Formula I wherein it is selected from:
N—{(S)-1-[(S)-3-Methyl-2-((S)-2-methylamino-propionylamino)-butyryl]-2,3-dihydro-1H-pyrrolo[2,3-b]pyridin-2-ylmethyl}-benzamide hydrochloride;
(S)—N—{(S)-1-[2-(Acetylamino-methyl)-2,3-dihydro-pyrrolo[2,3-b]pyridine-1-carbonyl]-2-methyl-propyl}-2-methylamino-propionamide hydrochloride;
(S)-2-Methylamino-N—((S)-2-methyl-1-{2-[(3-methyl-ureido)-methyl]-2,3-dihydro-pyrrolo[2,3-b]pyridine-1-carbonyl}-propyl)-propionamide hydrochloride;
(S)-2-Methylamino-N—{(S)-2-methyl-1-[(S)-2-(phenylacetylamino-methyl)-2,3-dihydro-pyrrolo[2,3-b]pyridine-1-carbonyl]-propyl}-propionamide hydrochloride;
(S)—N—{(S)-1-[(S)-2-(3,3-Dimethyl-ureidomethyl)-2,3-dihydro-pyrrolo[2,3-b]pyridine-1-carbonyl]-2-methyl-propyl}-2-methylamino-propionamide hydrochloride;

(S)-2-Methylamino-N—((S)-2-methyl-1-{(S)-2-[(3-phenyl-ureido)-methyl]-2,3-dihydro-pyrrolo[2,3-b]pyridine-1-carbonyl}-propyl)-propionamide hydrochloride; and
(S)-2-Methylamino-N—((S)-2-methyl-1-{(S)-2-[(2-phenyl-propionylamino)-methyl]-2,3-dihydro-pyrrolo[2,3-b]pyridine-1-carbonyl}-propyl)-propionamide hydrochloride;
or a pharmaceutically acceptable salt of any of the foregoing compounds.

One embodiment of the invention relates to compounds of Formula I wherein it is selected from:
(S)—N—{(S)-1-[(S)-2-(Methanesulfonylamino-methyl)-2,3-dihydro-pyrrolo[2,3-b]pyridine-1-carbonyl]-2-methyl-propyl}-2-methylamino-propionamide hydrochloride; and
(S)—N—{(S)-1-[(S)-2-(Benzenesulfonylamino-methyl)-2,3-dihydro-pyrrolo[2,3-b]pyridine-1-carbonyl]-2-methyl-propyl}-2-methylamino-propionamide hydrochloride; or
a pharmaceutically acceptable salt of any of the foregoing compounds.

One embodiment of the invention relates to compounds of Formula I wherein it is selected from:
{(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid methyl ester hydrochloride;
{(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid methyl ester hydrochloride; and
{(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid phenyl ester hydrochloride;
or a pharmaceutically acceptable salt of any of the foregoing compounds.

One embodiment of the invention relates to compounds of Formula I wherein it is selected from:
(S)-2-Methylamino-N—[(S)-2-methyl-1-((S)-2-phenylaminomethyl-2,3-dihydro-pyrrolo[2,3-b]pyridine-1-carbonyl)-propyl]-propionamide hydrochloride; and
(S)-2-Methylamino-N—{(S)-2-methyl-1-[(S)-2-(naphthalen-2-ylaminomethyl)-2,3-dihydro-pyrrolo[2,3-b]pyridine-1-carbonyl]-propyl}-propionamide hydrochloride;
or a pharmaceutically acceptable salt of any of the foregoing compounds.

One embodiment of the invention relates to a pharmaceutical composition comprising any of the compounds as described herein, or a pharmaceutically acceptable salt thereof, as an active ingredient together with a pharmaceutically acceptable carrier or excipient.

One embodiment of the invention relates to compounds of Formula I as described herein for use as a therapeutically active substance.

One embodiment of the invention relates to compounds of Formula I as described herein for use for the therapeutic and/or prophylactic treatment of cancer.

One embodiment of the invention relates to the use of a compound as described herein, or a pharmaceutically acceptable salt thereof, for the manufacture of a medicament for the therapeutic and/or prophylactic treatment of cancer.

One embodiment of the invention relates to a method of treating or ameliorating cancer comprising administering to a subject in need of such treatment a therapeutically effective amount of a compound as described herein.

One embodiment of the invention relates to compounds of Formula I wherein W is lower alkyl. In a particular embodiment W is methyl.

Another embodiment of the invention relates to compounds of Formula I wherein Y is lower alkyl. In a particular embodiment Y is methyl.

Another embodiment of the invention relates to compounds of Formula I where I where $R^1$ is lower alkyl, or a pharmaceutically acceptable salt thereof. In a particular embodiment $R^1$ is propanyl.

Another embodiment of the invention relates to compounds of Formula I where $R^2$ is lower akyl that is substituted with $NHC(O)R^6$, or a pharmaceutically acceptable salt thereof. In a particular embodiment, $R^2$ is methyl that is substituted with $NHC(O)R^6$ and $R^6$ is selected from aryl and lower alkyl, each of which may be substituted as define above, or a pharmaceutically acceptable salty thereof.

Another embodiment of the invention relates to compounds of Formula I where $R^2$ is lower akyl that is substituted with $NHSO_2R^5$, or a pharmaceutically acceptable salt thereof. In a particular embodiment, $R^2$ is methyl that is substituted with $NHSO_2R^5$ and $R^5$ is methyl or phenyl.

Another embodiment of the invention relates to compounds of Formula I where $R^2$ is lower akyl that is substituted with $NHCOOR^6$, or a pharmaceutically acceptable salt thereof. In a particular embodiment, $R^2$ is methyl that is substituted with $NHCOOR^6$ and $R^6$ is benzyl or methyl that optionally may be substituted with phenyl.

Another embodiment of the invention relates to compounds of Formula I where $R^2$ is lower akyl that is substituted with $NHR^6$, or a pharmaceutically acceptable salt thereof. In a particular embodiment $R^2$ is lower alkyl that is substituted with $NHR^6$ and $R^6$ is aryl, in particular phenyl or naphathanelyl, or a pharmaceutically acceptable salt thereof.

Another embodiment of the invention relates to compounds of Formula I where $R^3$ and $R^4$ are H, or a pharmaceutically acceptable salt thereof.

Another embodiment of the invention relates to compounds of Formula I where $R^5$ is lower alkyl or aryl. In a particular embodiment $R^5$ is methyl. In another embodiment $R^5$ is phenyl.

Another embodiment of the invention relates to compounds of Formula I where $R^6$ is phenyl that optionally may be substituted with lower alkyl, $OR^5$, halogen, $C(O)OR^5$, $C(O)NR^7R^8$, aryl, heterocyclyl, $C(O)R^9$, $SO_2R^5$, cyano and $CF_3$, or a pharmaceutically acceptable salt thereof.

Another embodiment of the invention relates to compounds of Formula I where $R^6$ is selected from lower alkyl and aryl, or a pharmaceutically acceptable salt thereof.

Another embodiment of the invention relates to compounds of Formula I where $R^6$ is $NR^7R^8$, or a pharmaceutically acceptable salt thereof. In a particular embodiment $R^7$ and $R^8$ are independently selected from H, methyl and phenyl.

Another embodiment of the invention relates to compounds of Formula I where W, Y and $R^1$ are lower alkyl, and $R^2$ is lower alkyl substituted by $NHCOR^6$ and $R^6$ is selected from a) phenyl, b) lower alkyl that optionally may be substituted with phenyl, c) $NR^7R^8$, and $R^7$ and $R^8$ are each independently selected from H, lower alkyl and phenyl, or a pharmaceutically acceptable salt thereof.

Another embodiment of the invention relates to compounds of Formula I where W, Y and $R^1$ are lower alkyl, $R^2$ is lower alkyl substituted by $NHSO_2R^5$, and $R^5$ is lower alkyl or phenyl, or a pharmaceutically acceptable salt thereof. In one embodiment $R^5$ is methyl. In another embodiment $R^5$ is phenyl.

Another embodiment of the invention relates to compounds of Formula I where W, Y and $R^1$ are lower alkyl, $R^2$ is lower alkyl substituted by $NHCOOR^6$ and $R^6$ is selected from a) aryl, b) lower alkyl that may be substituted with aryl, or a pharmaceutically acceptable salt thereof. In one embodiment $R^6$ is methyl that optionally may be substituted with phenyl. In another embodiment $R^6$ is phenyl.

Another embodiment of the invention relates to compounds of Formula I where W, Y and $R^1$ are lower alkyl, $R^2$ is lower alkyl substituted by $NHR^6$ and $R^6$ is aryl, or a pharmaceutically acceptable salt thereof. In one embodiment $R^6$ is phenyl. In another embodiment $R^6$ is naphthalenyl.

Compounds according to the invention wherein $R^2$ is lower alkyl that is substituted with $NHCOR^6$ include:
N—{(S)-1-[(S)-3-Methyl-2-((S)-2-methylamino-propionylamino)-butyryl]-2,3-dihydro-1H-pyrrolo[2,3-b]pyridin-2-ylmethyl}-benzamide hydrochloride (Example 1);
(S)—N—{(S)-1-[2-(Acetylamino-methyl)-2,3-dihydro-pyrrolo[2,3-b]pyridine-1-carbonyl]-2-methyl-propyl}-2-methylamino-propionamide hydrochloride (Example 2);
(S)-2-Methylamino-N—((S)-2-methyl-1-{2-[(3-methyl-ureido)-methyl]-2,3-dihydro-pyrrolo[2,3-b]pyridine-1-carbonyl}-propyl)-propionamide hydrochloride (Example 3);
(S)-2-Methylamino-N—{(S)-2-methyl-1-[(S)-2-(phenylacetylamino-methyl)-2,3-dihydro-pyrrolo[2,3-b]pyridine-1-carbonyl]-propyl}-propionamide hydrochloride (Example 4);
(S)—N—{(S)-1-[(S)-2-(3,3-Dimethyl-ureidomethyl)-2,3-dihydro-pyrrolo[2,3-b]pyridine-1-carbonyl]-2-methyl-propyl}-2-methylamino-propionamide hydrochloride (Example 6);
(S)-2-Methylamino-N—((S)-2-methyl-1-{(S)-2-[(3-phenyl-ureido)-methyl]-2,3-dihydro-pyrrolo[2,3-b]pyridine-1-carbonyl}-propyl)-propionamide hydrochloride (Example 7); and
(S)-2-Methylamino-N—((S)-2-methyl-1-{(S)-2-[(2-phenyl-propionylamino)-methyl]-2,3-dihydro-pyrrolo[2,3-b]pyridine-1-carbonyl}-propyl)-propionamide hydrochloride (Example 8); or a pharmaceutically acceptable salt of any of the foregoing compounds.

Compounds according to the invention wherein $R^2$ is lower alkyl that is substituted with $NHSO_2R^5$ include:
(S)—N—{(S)-1-[(S)-2-(Methanesulfonylamino-methyl)-2,3-dihydro-pyrrolo[2,3-b]pyridine-1-carbonyl]-2-methyl-propyl}-2-methylamino-propionamide hydrochloride (Example 9); and
(S)—N—{(S)-1-[(S)-2-(Benzenesulfonylamino-methyl)-2,3-dihydro-pyrrolo[2,3-b]pyridine-1-carbonyl]-2-methyl-propyl}-2-methylamino-propionamide hydrochloride (Example 10);
or a pharmaceutically acceptable salt of any of the foregoing compounds.

Compounds according to the invention wherein $R^2$ is lower alkyl that is substituted by $NHCOOR^6$ include:
{(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid methyl ester hydrochloride (Example 5);
{(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid methyl ester hydrochloride (Example 11); and
{(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid phenyl ester hydrochloride (Example 12);
or a pharmaceutically acceptable salt of any of the foregoing compounds.

Compounds according to the invention wherein $R^2$ is lower alkyl that is substituted by $NHR^6$ include:
(S)-2-Methylamino-N—[(S)-2-methyl-1-((S)-2-phenylaminomethyl-2,3-dihydro-pyrrolo[2,3-b]pyridine-1-carbonyl)-propyl]-propionamide hydrochloride (Example 13); and
(S)-2-Methylamino-N—{(S)-2-methyl-1-[(S)-2-(naphthalen-2-ylaminomethyl)-2,3-dihydro-pyrrolo[2,3-b]pyridine-1-carbonyl]-propyl}-propionamide hydrochloride (Example 14); or a pharmaceutically acceptable salt of any of the foregoing compounds.

The compounds of Formula I as well as their salts have at least one asymmetric carbon atom and therefore may be present as mixtures of different stereoisomers. The various isomers can be isolated by known separation methods, e.g., chromatography.

Compounds disclosed herein and covered by formula I above may exhibit tautomerism or structural isomerism. It is intended that the invention encompasses any tautomeric or structural isomeric form of these compounds, or mixtures of such forms, and is not limited to any one tautomeric or structural isomeric form depicted in the formulas above.

Dosages

The compounds of the invention preferably bind to BIR domains of an IAP preventing the IAP from binding to other proteins. Examples of Bir binding proteins include, but are not limited to, caspase 3, caspase 7, caspase 9, Smac and the like. Examples of IAPs include, but are not limited to, XIAP, cIAP1, cIAP2 or NAIP. In one aspect, the compound of the invention bind to the BIR2 and/or BIR3 domains of XIAP, cIAP1 and/or cIAP2. In another aspect, the compounds of the invention bind to the BIR2 domain of XIAP, cIAP1 and/or cIAP2.

Compounds of the invention are useful for inducing apoptosis in cells or sensitizing cells to apoptotic signals, in particular cancer cells. Apoptotic signals can be induced in cancer cells by, e.g., radiation therapy or antineoplastic chemotherapy. Alternatively, apoptotic signals can be induced in cancer cells by activation of the death receptors by death receptor agonists. Death receptor agonists can be naturally occurring, e.g., tumor necrosis factor α, (TNF-α) or non-naturally occurring, e.g., a synthetic antibody such as a DR4 or DR5 antibody.

The compounds of the present invention are thus useful in the amelioration, control or treatment of cell proliferative disorders such as, in particular, oncological disorders. These compounds and formulations containing said compounds are anticipated to be useful in the treatment or control of blood cancers, such as, for example, acute myeloid leukemia, or solid tumors, such as, for example, breast, colon, lung and prostate tumors.

A "therapeutically effective amount" or "effective amount" of a compound in accordance with this invention means an amount of compound that is effective to prevent, alleviate or ameliorate symptoms of disease or prolong the survival of the subject being treated. Determination of a therapeutically effective amount is within the skill in the art.

The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 10 mg to about 10,000 mg, preferably from about 200 mg to about 1,000 mg, should be appropriate, although the upper limit may be exceeded when indicated. The daily dosage can be administered as a single dose or in divided doses, or for parenteral administration, it may be given as one or more bolus injections or as a continuous infusion.

Pharmaceutical preparations useful in the practice of the invention, i.e., comprising the compounds of the invention can be administered internally, such as orally (e.g. in the form of tablets, coated tablets, dragées, hard and soft gelatin capsules, solutions, emulsions or suspensions), nasally (e.g. in the form of nasal sprays) or rectally (e.g. in the form of suppositories). However, the administration can also be effected parentally, such as intramuscularly or intravenously (e.g. in the form of injection solutions). Moreover, administration can be effected topically (e.g. in the form of ointments, creams or oils).

Compositions/Formulations

In an alternative embodiment, the present invention includes pharmaceutical compositions comprising at least one compound of formula I, or a pharmaceutically acceptable salt thereof, and a pharmaceutically acceptable excipient and/or carrier.

These pharmaceutical compositions can be suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, as well as the particular mode of administration. The amount of active ingredient which can be combined with a carrier material to produce a single dosage form will generally be that amount of a formula I compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

The compounds of Formula I and their pharmaceutically acceptable salts and esters can be processed with pharmaceutically inert, inorganic or organic adjuvants for the production of tablets, coated tablets, dragées and hard gelatin capsules. Lactose, polyvinylpyrrolidone, hydroxypropylmethylcellulose, hydroxypropylcellulose, microcrystalline cellulose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc. Suitable adjuvants for the production of solutions and syrups are, for example, H₂O, polyols, saccharose, invert sugar, glucose, etc.

Suitable adjuvants for injection solutions are, for example, H$_2$O, alcohols, polyols, glycerol, vegetable oils, etc. Suitable adjuvants for suppositories are, for example, natural or hardened oils, waxes, fats, semi-solid or liquid polyols, etc. Suitable adjuvants for topical preparations are glycerides, semi-synthetic and synthetic glycerides, hydrogenated oils, liquid waxes, liquid paraffins, liquid fatty alcohols, sterols, polyethylene glycols and cellulose derivatives.

Moreover, the pharmaceutical preparations can contain preservatives, solubilizers, viscosity-increasing substances, stabilizers, wetting agents, emulsifiers, sweeteners, colorants, flavors, salts for varying the osmotic pressure, buffers, masking agents or antioxidants. They can also contain other therapeutic substances.

The compounds in the present invention (compounds of general Formula I) can be prepared using the general reaction scheme set out in the schemes below.

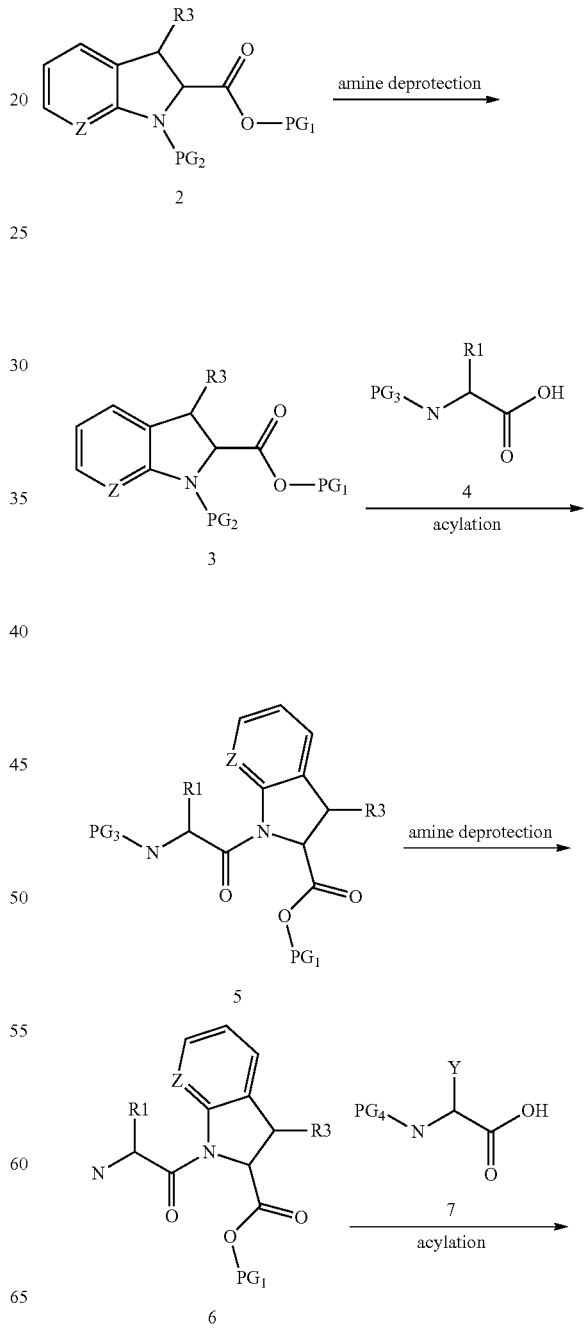

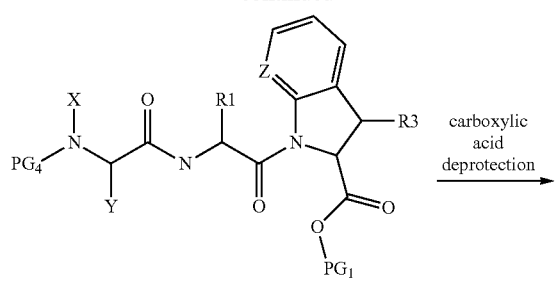

8

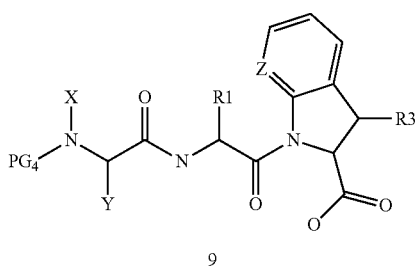

9

The amine protecting group PG2 of a suitably protected indoline or azaindoline of general structure 2 can be removed to afford compounds of general formula 3. Compounds of general formula 3 can be acylated with compounds of general formula 4 to give compounds of general formula 5. The acylation methods include, but are not limited to, acyl halides, acyl azides, and standard peptide coupling reagents. The amine protecting group PG3 in compounds of general formula 5 can be removed to afford compounds of general formula 6. Compounds of general formula 6 can be acylated with compounds of general formula 7 to give compounds of general formula 8. The acylation methods include, but are not limited to, standard peptide coupling reagents. The carboxylic acid protecting group PG1 of compounds of general structure 8 can be removed to form compounds of general structure 9.

Schem 1b

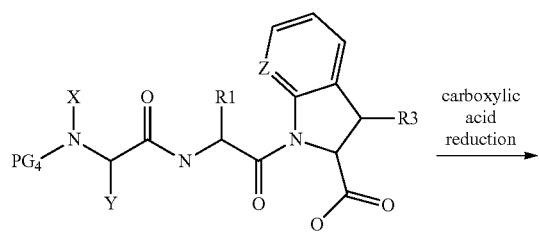

9

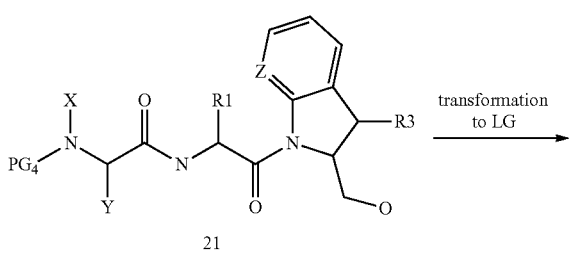

21

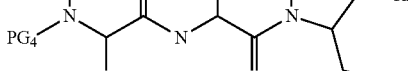

22

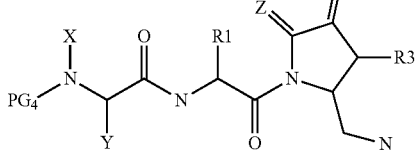

23

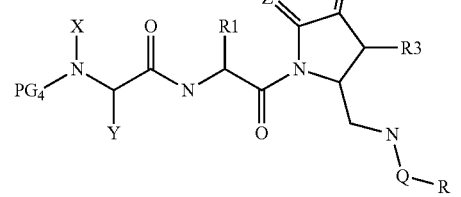

25

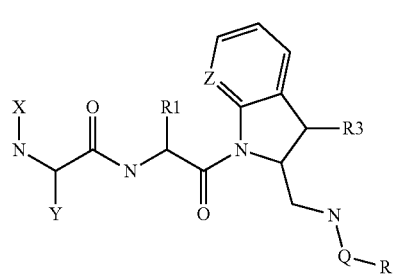

26

The carboxylic acid group of a suitably protected indoline or azaindoline of general structure 9 can then be reduced to afford compounds of general formula 21. Reduction methods included, but are not limited to, the conversion of the acid to the acyl chloride or mixed anhydride and subsequent treatment with sodium borohydride. The hydroxyl group of compounds of general formula 21 can be converted to an appropriate leaving group to give compounds of general formula 22. Methods for this conversion include treatment with methansulfonyl chloride or toluenesulfonyl chloride. Compounds of general formula 22 can be converted to amines of general formula 23 by treatment with an appropriate nitrogen nucleophile and subsequent unmasking of the primary amine moiety. Methods for this transformation include the use of sodium azide followed by reduction to the amine. The amine moiety of compounds of general formula 23 can be acylated or sulfonylated with compounds of general formula 24, where Q is CO or $SO_2$, to give compounds of general formula 25. The amine protecting group PG4 can be then removed to afford compounds of general formula 26.

Scheme 2

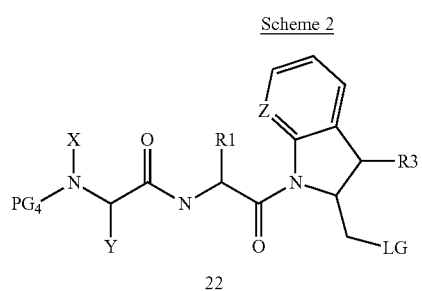

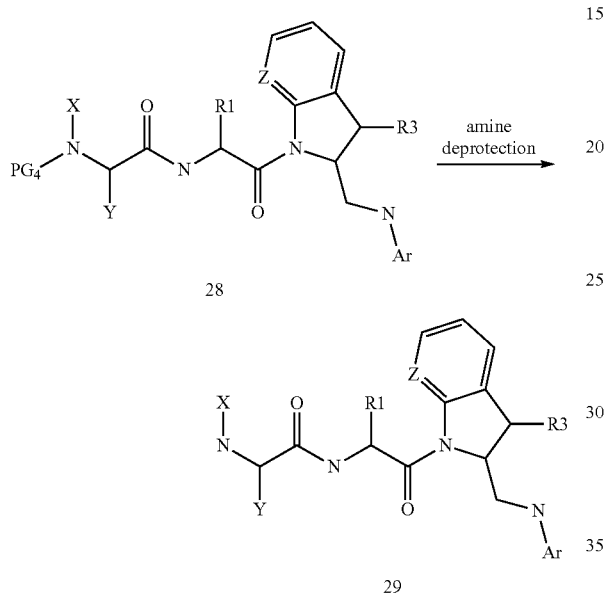

Compounds of general formula 22 can be converted to amines of general formula 28 by treatment with an appropriate aromatic nitrogen nucleophile. The amine protecting group PG4 can be then removed to afford compounds of general formula 29.

Scheme 3

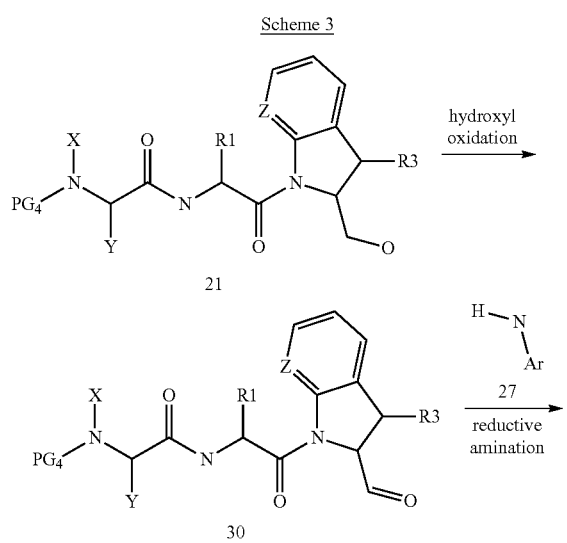

Compounds of general formula 21 can be oxidized to compounds of general formula 30 with standard oxidation reagents. Compounds of general formula 30 can be converted to amines of general formula 28 by treatment with an appropriate aromatic nitrogen nucleophile of formula 27 under reducing conditions. The amine protecting group PG4 can be then removed to afford compounds of general formula 29.

Methods to perform the above described reactions and processes would be apparent to those of ordinary skill in the art based on the present disclosure, or can be deduced in analogy from the examples. Starting materials are commercially available or can be made by methods analogous to those described in the Examples below.

Crystal Forms

When the compounds of the invention are solids, it is understood by those skilled in the art that these compounds, and their salts, may exist in different crystal or polymorphic forms, all of which are intended to be within the scope of the present invention and specified formulas.

EXAMPLES

The compounds of the present invention may be synthesized according to known techniques. The following examples and references are provided to aid the understanding of the present invention. The examples are not intended, however, to limit the invention, the true scope of which is set forth in the appended claims. The names of the final products in the examples were generated using AutoNom 2000 Add-in v4.0 SP2 (function in ISIS Draw, Elsevier/MDL), or AutoNom 2000 TT v4.01.305 (Elsevier/MDL), or functions available in ChemDraw Pro Control 11.0.2 (CambridgeSoft Corp.), or Struct=Name feature of electronic notebooks.

Preparation of Intermediates

Intermediate 1

(S)-1-{(S)-2-[(S)-2-(tert-Butoxycarbonyl-methyl-amino)-propionylamino]-3-methyl-butyryl}-2,3-dihydro-1H-pyrrolo[2,3-b]pyridine-2-carboxylic acid

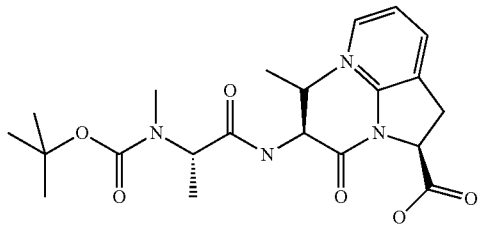

Step 1: To a solution of (S)-2-(tert-butoxycarbonylamino)-3-methylbutanoic acid (6.3 g, 29.0 mmol, Eq: 1.00) in DCM at rt was added pyridine (4.01 g, 4.1 mL, 50.7 mmol, Eq: 1.75) followed by cyanuric fluoride (5.98 g, 3.8 mL, 44.3 mmol, Eq: 1.53). The resulting mixture was stirred at rt for 2 h. Ice (160 mL) was added and the resulting mixture was stirred rapidly for 15 min. The resulting mixture was filtered through a coarse frit funnel, using DCM (2×60 mL) to wash the precipitate. The combined filtrate was put into a separatory funnel and the layers were separated. The aqueous layer was extracted with DCM (1×50 mL) and then the combined organic layers were washed with ice-cold water (2×100 mL), dried briefly over Na$_2$SO$_4$, then concentrated in vacuo to a volume of ~20 mL. This solution was added to a solution of ethyl(R,S)-2,3-dihydro-1H-pyrrolo[2,3-b]pyridine-2-carboxylate (2.7 g, 14.0 mmol, Eq: 1.00) and N-methylmorpholine (5.7 g, 6.2 mL, 56.4 mmol, Eq: 4.01) in DCM (50 mL) and the reaction mixture was stirred at rt overnight. The reaction mixture was diluted with EtOAc (200 mL) and washed with 0.1 M aqueous KHSO$_4$. The aqueous layer was back-extracted with EtOAc (50 mL at a time) to until all product was in the EtOAc layer. The combined EtOAc layers were concentrated to ~250 mL, washed with 0.2 M aqueous NaOH and brine and concentrated in vacuo. The crude material was purified by flash chromatography (silica gel, 80 g, 0% to 30% EtOAc in hexanes). The material obtained was taken up in EtOAc/hexanes (~200 mL), washed with 0.1 M NaOH, and concentrated in vacuo to give the racemic desired product (4.48 g) as a colorless viscous oil. The diastereomers were then separated by flash chromatography (silica gel, 120 g, 0% to 20 EtOAc/toluene) to give (S)-ethyl 1-((S)-2-(tert-butoxycarbonylamino)-3-methylbutanoyl)-2,3-dihydro-1H-pyrrolo [2,3-b]pyridine-2-carboxylate (1.9 g) and (R)-ethyl 1-((S)-2-(tert-butoxycarbonylamino)-3-methylbutanoyl)-2,3-dihydro-1H-pyrrolo[2,3-b]pyridine-2-carboxylate (2.1 g), m/z=392 (M+H).

Step 2: To a solution of (S)-ethyl 1-((S)-2-(tert-butoxycarbonylamino)-3-methylbutanoyl)-2,3-dihydro-1H-pyrrolo[2,3-b]pyridine-2-carboxylate (1.9 g, 4.85 mmol, Eq: 1.00) in EtOH (10.1 mL) was added HCl (2 M in ether, 38.0 mL, 76.0 mmol, Eq: 15.7) and the resulting solution was stirred at rt overnight. The reaction mixture was concentrated in vacuo and azeotroped with n-heptane (1×75 mL) to give (S)-ethyl 1-((S)-2-amino-3-methylbutanoyl)-2,3-dihydro-1H-pyrrolo[2,3-b]pyridine-2-carboxylate hydrochloride as a white solid (1.6 g).

Step 3: To a solution of (S)-ethyl 1-((S)-2-amino-3-methylbutanoyl)-2,3-dihydro-1H-pyrrolo[2,3-b]pyridine-2-carboxylate hydrochloride (1.6 g, 4.88 mmol, Eq: 1.00) in DMF (20 mL) was added (S)-2-(tert-butoxycarbonyl(methyl)amino)propanoic acid (1.2 g, 5.9 mmol, Eq: 1.21) and HATU (2.2 g, 5.79 mmol, Eq: 1.19). Diisopropylethylamine (1.63 g, 2.2 mL, 12.6 mmol, Eq: 2.58) was then added and the resulting yellow solution was stirred at rt for 1 h. The reaction mixture was diluted with EtOAc (100 mL) and hexanes (50 mL) and washed with 0.1 M aqueous KHSO$_4$, 0.1 M aqueous NaOH, and brine and concentrated in vacuo. The crude material was purified by flash chromatography (silica gel, 80 g, 0% to 20% EtOAc/(DCM:hexanes 1:1) then 20% to 40% EtOAc/(DCM:hexanes 1:1) after first spot has eluted) to give (S)-ethyl 1-((S)-2-((S)-2-(tert-butoxycarbonyl(methyl)amino)propanamido)-3-methylbutanoyl)-2,3-dihydro-1H-pyrrolo [2,3-b]pyridine-2-carboxylate (1.9 g), m/z=477 (M+H).

Step 4: A solution of (S)-ethyl 1-((S)-2-((S)-2-(tert-butoxycarbonyl(methyl)amino)propanamido)-3-methylbutanoyl)-2,3-dihydro-1H-pyrrolo[2,3-b]pyridine-2-carboxylate (1.9 g, 3.99 mmol, Eq: 1.00) in THF (36 mL) and MeOH (12 mL) was cooled in an ice bath. To this solution was added a solution of lithium hydroxide monohydrate (0.5 g, 11.9 mmol, Eq: 2.99) in water (12 mL) and the cooling bath was removed. After 1 h, the reaction was quenched by adding 0.1 M aqueous KHSO$_4$ (200 mL) and the mixture was extracted with DCM (2×100 mL). The combined DCM layers were dried over Na$_2$SO$_4$ and concentrated in vacuo. The residue was azeotroped with n-heptane (1×100 mL) to give of (S)-1-((S)-2-((S)-2-(tert-butoxycarbonyl(methyl)amino)propanamido)-3-methylbutanoyl)-2,3-dihydro-1H-pyrrolo[2,3-b] pyridine-2-carboxylic acid (1.8 g) as a white solid, m/z=449 (M+H).

Intermediate 2

Toluene-4-sulfonic acid (S)-1-{(S)-2-[(S)-2-(tert-butoxycarbonyl-methyl-amino)-propionylamino]-3-methyl-butyryl}-2,3-dihydro-1H-pyrrolo[2,3-b]pyridin-2-ylmethyl ester

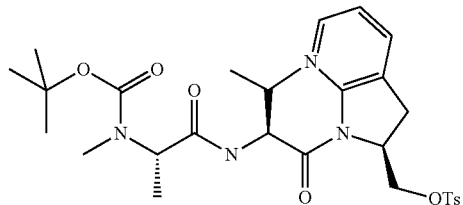

Step 1: To a stirred solution of 1-{(S)-2-[(S)-2-(tert-butoxycarbonyl-methyl-amino)-propionyl amino]-3-methyl-butyryl}-2,3-dihydro-1H-pyrrolo[2,3-b]pyridine-2-carboxylic acid (Intermediate 1) (3.8 g, 8.48 mmol) in THF (65 mL) were added N-methylmorpholine (1.11 mL, 10.17 mmol) followed by the addition of isobutyl chloroformate (1.32 mL, 10.17 mmol) at −20° C. The reaction mixture was stirred at −20° C. for 10 min and the white precipitate of N-methylmorpholine hydrochloride salt was removed by filtration. The filtrate was cooled to −20° C., NaBH$_4$ (483 mg, 12.72 mmol) was added followed by cold water (30 mL) at −20° C. After 30 min the reaction mixture was poured into water (25 mL) and extracted with ethyl acetate (80 mL×2). The combined organic layers were washed with water, brine, dried over Na$_2$SO$_4$ and concentrated in vacuo. The resulting residue was purified by flash chromatography (silica gel, 28% EtOAc in hexanes) to give {(S)-1-[(S)-1-(2-hydroxymethyl-2,3-dihydro-pyrrolo[2,3-b]pyridine-1-carbonyl)-2-methyl-propylcarbamoyl]-ethyl}-methyl-carbamic acid tert-butyl ester (2.7 g), m/z=435 (M+H)

Step 2: To a solution of {(S)-1-[(S)-1-(2-hydroxymethyl-2,3-dihydro-pyrrolo[2,3-b]pyridine-1-carbonyl)-2-methyl-propylcarbamoyl]-ethyl}-methyl-carbamic acid tert-butyl ester (4.5 g, 10.36 mmol) in DCM (150 mL), was added triethylamine (4.25 mL, 31.106 mmol) followed by the slow addition of tosyl chloride (3.0 g, 15.55 mmol) at 0° C. The reaction mixture was stirred at rt for 16 h and then the reaction mixture was concentrated in vacuo. Water was added to the residue and the resulting mixture was extracted with EtOAc (300 mL×2). The combined organic layers were dried (Na$_2$SO$_4$) and concentrated in vacuo. The resulting residue was purified by flash chromatography (silica gel, 18% EtOAc in hexanes) to give toluene-4-sulfonic acid (S)-1-{(S)-2-[(S)-2-(tert-butoxycarbonyl-methyl-amino)-propionylamino]-3-methyl-butyryl}-2,3-dihydro-1H-pyrrolo[2,3-b]pyridin-2-ylmethyl ester (2.7 g) and toluene-4-sulfonic acid (R)-1-{(S)-2-[(S)-2-(tert-butoxycarbonyl-methyl-amino)-propionylamino]-3-methyl-butyryl}-2,3-dihydro-1H-pyrrolo[2,3-b]pyridin-2-ylmethyl ester (1 g), m/z=589 (M+H).

Intermediate 3

{(S)-1-[(S)-1-((S)-2-aminomethyl-2,3-dihydro-pyrrolo[2,3-b]pyridine-1-carbonyl)-2-methyl-propylcarbamoyl]-ethyl}-methyl-carbamic acid tert-butyl ester

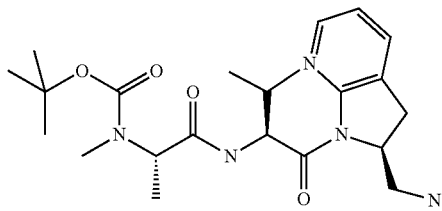

Step 1: To a stirred solution of toluene-4-sulfonic acid (S)-1-{(S)-2-[(S)-2-(tert-butoxycarbonyl-methyl-amino)-propionylamino]-3-methyl-butyryl}-2,3-dihydro-1H-pyrrolo[2,3-b]pyridin-2-ylmethyl ester (Intermediate 2) (200 mg, 0.34 mmol) in DMF (4 mL) was added NaN$_3$ (26.53 mg, 0.408 mmol) and the resulting mixture was heated at 90° C. for 3 h. The reaction was concentrated in vacuo and the obtained residue was dissolved in ethyl acetate (25 mL) and washed with water and brine, dried (Na$_2$SO$_4$) and concentrated in vacuo. The resulting residue was purified by flash chromatography (silica gel, 12% EtOAc in hexanes) to give {(S)-1-[(S)-1-((S)-2-azidomethyl-2,3-dihydro-pyrrolo[2,3-b]pyridine-1-carbonyl)-2-methyl-propylcarbamoyl]-ethyl}-methyl-carbamic acid tert-butyl ester (140 mg), m/z=460 (M+H).

Step 2: A mixture of {(S)-1-[(S)-1-((S)-2-azidomethyl-2,3-dihydro-pyrrolo[2,3-b]pyridine-1-carbonyl)-2-methyl-propylcarbamoyl]-ethyl}-methyl-carbamic acid tert-butyl ester (550 mg) and 10% palladium on carbon in methanol (4 mL) was stirred under a hydrogen atmosphere (balloon) for 2 h. The reaction mixture was filtered through a Celite pad and the filtrate was evaporated to dryness to give {(S)-1-[(S)-1-((S)-2-aminomethyl-2,3-dihydro-pyrrolo[2,3-b]pyridine-1-carbonyl)-2-methyl-propylcarbamoyl]-ethyl}-methyl-carbamic acid tert-butyl ester (470 mg), m/z=434 (M+H).

Example 1

N—{(S)-1-[(S)-3-Methyl-2-((S)-2-methylamino-propionylamino)-butyryl]-2,3-dihydro-1H-pyrrolo[2,3-b]pyridin-2-ylmethyl}-benzamide, hydrochloride

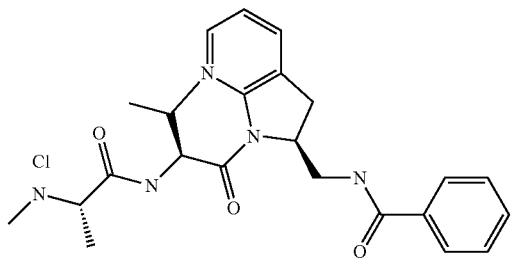

Step 1: A solution of {(S)-1-[(S)-1-((S)-2-aminomethyl-2,3-dihydro-pyrrolo[2,3-b]pyridine-1-carbonyl)-2-methyl-propylcarbamoyl]-ethyl}-methyl-carbamic acid tert-butyl ester (intermediate 3) (100 mg 0.23 mmol) in DCM (4 mL) was cooled to 0-5° C. and triethylamine (0.08 mL 0.57 mmol) followed by benzoyl chloride (0.027 mL, 0.23 mmol) were added. The reaction was stirred at rt for 4 h. The reaction mixture was partitioned between water and DCM and the organic layer was then washed with water (30 mL×2) and brine (30 mL). The combined organic layers were dried over Na$_2$SO$_4$ and concentrated in vacuo. The resulting residue was purified by preparative-HPLC (acetonitrile and NH$_4$OAc] to give ((S)-1-{(S)-1-[(S)-2-(benzoylamino-methyl)-2,3-dihydro-pyrrolo[2,3-b]pyridine-1-carbonyl]-2-methyl-propyl-carbamoyl}-ethyl)-methyl-carbamic acid tert-butyl ester as a white solid (35 mg), m/z=538 (M+H).

Step 2: To a solution of ((S)-1-{(S)-1-[(S)-2-(benzoylamino-methyl)-2,3-dihydro-pyrrolo[2,3-b]pyridine-1-carbonyl]-2-methyl-propylcarbamoyl}-ethyl)-methyl-carbamic acid tert-butyl ester (30 mg, 0.056 mmol) in dioxane (0.5 mL) was added dropwise 4 M HCl in dioxane (0.3 mL) at 0° C. The reaction mixture was stirred for 2 h at rt and then the solvent removed in vacuo. Trituration of the residue with hexane gave N—{(S)-1-[(S)-3-Methyl-2-((S)-2-methylamino-propionylamino)-butyryl]-2,3-dihydro-1H-pyrrolo[2,3-b]pyridin-2-ylmethyl}-benzamide, hydrochloride as an off white solid (25 mg), m/z=438 (M+H).

The following examples in Table 1 were prepared using the same procedures as for Example 1 with the noted reactant modifications.

TABLE 1

| EX # | Step 1 Acylating or sulfonylating Agent | m/z (M + H) |
|---|---|---|
| 2 | acetyl chloride | 376 |
| 3 | N-methylcarbamoyl chloride | 391 |
| 4 | benzoyl chloride | 452 |
| 5 | methyl chloroformate | 392 |
| 6 | N,N-dimethyl-carbamoyl chloride | 405 |

TABLE 1-continued

| EX # | Step 1 Acylating or sulfonylating Agent | m/z (M + H) |
|---|---|---|
| 7 | phenyl isocyanate | 453 |
| 8 | 2-phenyl-propionyl chloride | 466 |
| 9 | methanesulfonyl chloride | 412 |
| 10 | benzenesulfonyl chloride | 472 |

TABLE 1-continued

| EX # | | Step 1 Acylating or sulfonylating Agent | m/z (M + H) |
|---|---|---|---|
| 11 | 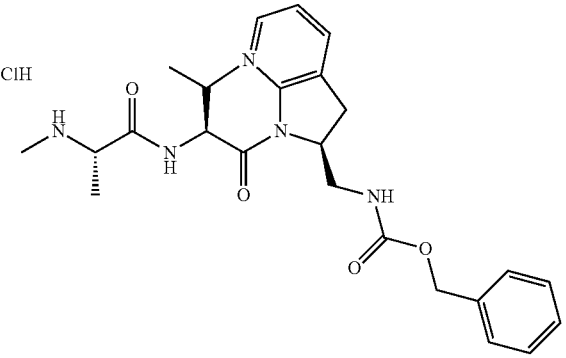 | benzyl chloroformate | 468 |
| 12 | 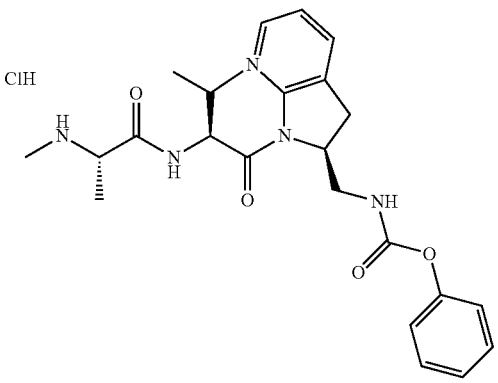 | phenyl chloroformate | 454 |

Example 13

(S)-2-Methylamino-N—[(S)-2-methyl-1-((S)-2-phenylaminomethyl-2,3-dihydro-pyrrolo[2,3-b]pyridine-1-carbonyl)-propyl]-propionamide, hydrochloride

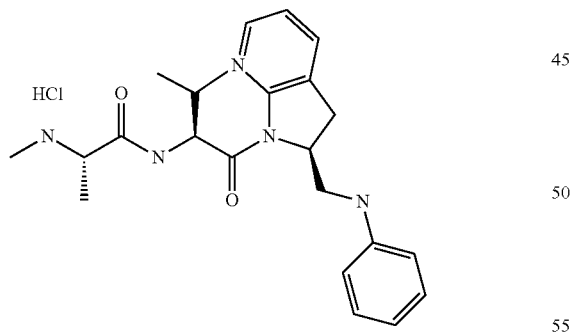

Step 1: To the stirred solution of toluene-4-sulfonic acid (S)-1-{(S)-2-[(S)-2-(tert-butoxycarbonyl-methyl-amino)-propionylamino]-3-methyl-butyryl}-2,3-dihydro-1H-pyrrolo[2,3-b]pyridin-2-ylmethyl ester (Intermediate 2) (50 mg, 0.085 mmol) in 1,4-dioxane (0.5 mL), K₂CO₃ (29.3 mg, 0.127 mmol), was added aniline (0.012 mL, 0.127 mmol) and the reaction mixture irradiated in a microwave at 125° C. for 1 h. The reaction mixture was diluted with DCM (10 mL), washed with water and brine and the separated organic layer was concentrated in vacuo. The crude product was purified by preparative HPLC (X Bridge Prep C18 (250×19.0 mm) 5µ, acetonitrile and 0.05% formic acid) to give methyl-{(S)-1-[(S)-2-methyl-1-((S)-2-phenylaminomethyl-2,3-dihydro-pyrrolo[2,3-b]pyridine-1-carbonyl)-propylcarbamoyl]-ethyl}-carbamic acid tert-butyl ester (30 mg), m/z=510.6 (M+H).

To a solution of methyl-{(S)-1-[(S)-2-methyl-1-((S)-2-phenylaminomethyl-2,3-dihydro-pyrrolo[2,3-b]pyridine-1-carbonyl)-propylcarbamoyl]-ethyl}-carbamic acid tert-butyl ester (25 mg, 0.05 mmol) in 1,4-dioxane (0.5 mL) was added 4 M HCl in dioxane (0.5 mL) dropwise at 0° C. The reaction mixture was stirred at rt for 3 h then concentrated in vacuo to obtain (S)-2-methylamino-N—[(S)-2-methyl-1-((S)-2-phenylaminomethyl-2,3-dihydro-pyrrolo[2,3-b]pyridine-1-carbonyl)-propyl]-propionamide hydrochloride (18 mg), m/z=410.4 (M+H).

Example 14

(S)-2-methylamino-N—{(S)-2-methyl-1-[(S)-2-(naphthalen-2-ylaminomethyl)-2,3-dihydro-pyrrolo[2,3-b]pyridine-1-carbonyl]-propyl}-propionamide hydrochloride

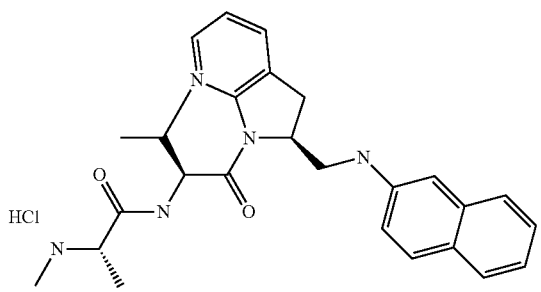

Step 1: To a stirred solution of 1-{(S)-2-[(S)-2-(tert-butoxycarbonyl-methyl-amino)-propionyl amino]-3-methyl-butyryl}-2,3-dihydro-1H-pyrrolo[2,3-b]pyridine-2-carboxylic acid (Intermediate 1) (3.8 g, 8.48 mmol) in THF (65 mL) were added N-methylmorpholine (1.11 mL, 10.17 mmol) followed by the addition of isobutyl chloroformate (1.32 mL, 10.17 mmol) at −20° C. The reaction mixture was stirred at −20° C. for 10 min and the white precipitate of N-methylmorpholine hydrochloride salt was removed by filtration. The filtrate was cooled to −20° C., NaBH$_4$ (483 mg, 12.72 mmol) was added followed by cold water (30 mL) at −20° C. After 30 min the reaction mixture was poured into water (25 mL) and extracted with ethyl acetate (80 mL×2). The combined organic layers were washed with water, brine, dried over Na$_2$SO$_4$ and concentrated in vacuo. The resulting residue was purified by flash chromatography (silica gel, 28% EtOAc in hexanes) to give {(S)-1-[(S)-1-(2-hydroxymethyl-2,3-dihydro-pyrrolo[2,3-b]pyridine-1-carbonyl)-2-methyl-propylcarbamoyl]-ethyl}-methyl-carbamic acid tert-butyl ester (2.7 g), m/z=435 (M+H)

Step 2: To {(S)-1-[(S)-1-(2-hydroxymethyl-2,3-dihydro-pyrrolo[2,3-b]pyridine-1-carbonyl)-2-methyl-propylcarbamoyl]-ethyl}-methyl-carbamic acid tert-butyl ester (16.5 mg, 0.038 mmol) in DCM (0.4 mL) at 0° C. was added sequentially KBr (3.1 g, 0.027 mmol), TEMPO (0.3 mg) and 8% NaOCl solution (0.35 mL, 10 eq) and the reaction was stirred vigorously for 1 h. The reaction mixture was diluted with DCM and washed with water and brine and then concentrated in vacuo to give {(S)-1-[(S)-1-((S)-2-formyl-2,3-dihydro-pyrrolo[2,3-b]pyridine-1-carbonyl)-2-methyl-propylcarbamoyl]-ethyl}-methyl-carbamic acid tert-butyl ester (12 mg).

Step 3: To a stirred solution of {(S)-1-[(S)-1-((S)-2-formyl-2,3-dihydro-pyrrolo[2,3-b]pyridine-1-carbonyl)-2-methyl-propylcarbamoyl]-ethyl}-methyl-carbamic acid tert-butyl ester (30 mg, 0.07 mmol) in dry MeOH (1.0 mL) was added 2-napthylamine (20 mg, 0.14 mmol) was the reaction was stirred at rt for 18 h. Acetic acid was added to adjust to pH ~4. NaCNBH$_3$ (8.7 mg, 0.139 mmol) was added and the reaction was stirred at rt for 18 h. The reaction mixture was concentrated in vacuo. The residue was taken up in EtOAc (25 mL) and washed with saturated aqueous NaHCO$_3$ (10 mL×2), water (10 mL×2) and brine (4 mL×2) and concentrated in vacuo. The crude material was purified by preparative HPLC (X Bridge Prep C18 (250×19 0 mm) 5μ, acetonitrile and 5 mM NH$_4$OAc) to give methyl-((S)-1-{(S)-2-methyl-1-[(S)-2-(naphthalen-2-ylaminomethyl)-2,3-dihydro-pyrrolo[2,3-b]pyridine-1-carbonyl]-propylcarbamoyl}-ethyl)-carbamic acid tert-butyl ester (32 mg), m/z=560 (M+H).

Step 4: To a solution of methyl-((S)-1-{(S)-2-methyl-1-[(S)-2-(naphthalen-2-ylaminomethyl)-2,3-dihydro-pyrrolo[2,3-b]pyridine-1-carbonyl]-propylcarbamoyl}-ethyl)-carbamic acid tert-butyl ester (27 mg, 0.05 mmol) in 1,4-dioxane (0.5 mL) was added 4 M HCl in dioxane (0.5 mL) dropwise at 0° C. The reaction mixture was stirred at rt for 3 h and then the solvent was removed in vacuo to give (S)-2-methylamino-N—{(S)-2-methyl-1-[(S)-2-(naphthalen-2-ylaminomethyl)-2,3-dihydro-pyrrolo[2,3-b]pyridine-1-carbonyl]-propyl}-propionamide hydrochloride (23 mg), m/z=460 (M+H).

Example 15

Biochemical Assays

TR-FRET Assay for BIR2 and BIR3

The ability of a test compound to inhibit the binding of BIR2 and/or BIR3 domains of the XIAP protein to Peptide A (a SMAC-derived peptide described below) evidences that the test compound acts as a SMAC-mimetic resulting in reactivation of a cell's apoptotic pathway.

The peptide AVPIAQKSEK-(ε-biotin)-OH 1:2 TFA ("Peptide A") was identified as a substrate for the TR-FRET assay by screening the 6× Histidine-tagged BIR2 domain and BIR3 domain of XIAP against a set of 29 peptides synthesized based on sequences reported by Sweeny et al. (*Biochemistry*, 2006, 45, 14740 14748). The peptides were labeled with the fluorescent tags FITC or TAMRA and Kd values were determined by fluorescence polarization assay. The sequence AVPIAQKSEK was identified as optimal for using in an assay. The peptide sequence was derivatized with biotin to provide AVPIAQKSEK-(ε-biotin)-OH 1:2 TFA as the substrate for the TR-FRET assay.

The XIAP protein sequence was obtained from the SWISS-PROT protein sequence database and the BIR2 and BIR3 domains were derived from that. The sequence of the BIR2 domain used for the TR-FRET assay is MRHHHHH-HRDHFALDRPSETHADYLLRTGQVVDIS-DTIYPRNPAMYSEEARLKSF QNWPDYAHLTPRELA-SAGLYYTGIGDQVQCFACGGKLKNWEPG DRAWSEHRRHE PNCFFVLGRNLNIRSE.

The sequence of the BIR3 domain used for the TR-FRET assay is MRHHHHHHRSDAVSSDRNFPNSTNL-PRNPSMADYEARIFTEGTWIYSVNK EQLARAGFYALGEGDKVKCFHCGGGLTD-WKPSEDPWEQHAKWYPGCKYL L EQKGQEYINNIHLTHSLEECLVRTT.

Ten nanomolar of 6× Histidine-tagged BIR2 domain, corresponding to amino acids 124-240 of XIAP, or BIR3 domain, corresponding to amino acids 241-356 of XIAP, was mixed with 20 nM of the peptide AVPIAQKSEK-(ε-biotin)-OH 1:2 TFA, in the presence of 50 mM Tris-Cl, pH 7.5, 100 mM NaCl, 1 mM dithiothreitol (DTT) and 0.1 mg/mL bovine serum albumin (BSA). Following a 45 mM incubation at 37° C., Europium-Streptavidin and Allophycocyanin conjugated anti-Histidine antibody were added to a final concentration of 1.5 nM and 15 nM, respectively. Time-resolved fluorescence resonance energy transfer (TR-FRET) signals were measured 1 hour later at room temperature. Test compound potency was assessed at 10 serially diluted concentrations. Percentage of inhibition at each concentration was determined to generate an IC$_{50}$ value for each test compound.

These values are listed below in Table 2.

TABLE 2

| EX | Systematic Name | Ic50 BIR2 | Ic50 BIR3 |
|---|---|---|---|
| 1 | N-{(S)-1-[(S)-3-Methyl-2-((S)-2-methylamino-propionylamino)-butyryl]-2,3-dihydro-1H-pyrrolo[2,3-b]pyridin-2-ylmethyl}-benzamide hydrochloride | 0.888 | 52.98 |
| 2 | (S)-N-{(S)-1-[2-(Acetylamino-methyl)-2,3-dihydro-pyrrolo[2,3-b]pyridine-1-carbonyl]-2-methyl-propyl}-2-methylamino-propionamide hydrochloride | 4.665 | >54.8 |
| 3 | (S)-2-Methylamino-N-((S)-2-methyl-1-{2-[(3-methyl-ureido)-methyl]-2,3-dihydro- | 4.875 | >54.8 |

TABLE 2-continued

| EX | Systematic Name | Ic50 BIR2 | Ic50 BIR3 |
|---|---|---|---|
| | pyrrolo[2,3-b]pyridine-1-carbonyl}-propyl)-propionamide hydrochloride | | |
| 4 | (S)-2-Methylamino-N-{(S)-2-methyl-1-[(S)-2-(phenylacetylamino-methyl)-2,3-dihydro-pyrrolo[2,3-b]pyridine-1-carbonyl]-propyl}-propionamide hydrochloride | 1.57 | >54.8 |
| 5 | {(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid methyl ester hydrochloride | 1.669 | >54.8 |
| 6 | (S)-N-{(S)-1-[(S)-2-(3,3-Dimethyl-ureidomethyl)-2,3-dihydro-pyrrolo[2,3-b]pyridine-1-carbonyl]-2-methyl-propyl}-2-methylamino-propionamide hydrochloride | 6.167 | >54.8 |
| 7 | (S)-2-Methylamino-N-((S)-2-methyl-1-{(S)-2-[(3-phenyl-ureido)-methyl]-2,3-dihydro-pyrrolo[2,3-b]pyridine-1-carbonyl}-propyl)-propionamide hydrochloride | 1.544 | >54.8 |
| 8 | (S)-2-Methylamino-N-((S)-2-methyl-1-{(S)-2-[(2-phenyl-propionylamino)-methyl]-2,3-dihydro-pyrrolo[2,3-b]pyridine-1-carbonyl}-propyl)-propionamide hydrochloride | 2.561 | >54.8 |
| 9 | (S)-N-{(S)-1-[(S)-2-(Methanesulfonylamino-methyl)-2,3-dihydro-pyrrolo[2,3-b]pyridine-1-carbonyl]-2-methyl-propyl}-2-methylamino-propionamide hydrochloride | 1.236 | >54.8 |
| 10 | (S)-N-{(S)-1-[(S)-2-(Benzenesulfonylamino-methyl)-2,3-dihydro-pyrrolo[2,3-b]pyridine-1-carbonyl]-2-methyl-propyl}-2-methylamino-propionamide hydrochloride | 0.82 | >54.8 |
| 11 | {(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid benzyl ester | 1.047 | >54.8 |
| 12 | {(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid phenyl ester hydrochloride | 1.622 | >54.8 |
| 13 | (S)-2-Methylamino-N-[(S)-2-methyl-1-((S)-2-phenylaminomethyl-2,3-dihydro-pyrrolo[2,3-b]pyridine-1-carbonyl)-propyl]-propionamide hydrochloride | 0.307 | 5.343 |
| 14 | (S)-2-Methylamino-N-{(S)-2-methyl-1-[(S)-2-(naphthalen-2-ylaminomethyl)-2,3-dihydro-pyrrolo[2,3-b]pyridine-1-carbonyl]-propyl}-propionamide hydrochloride | 0.506 | 3.952 |

The invention claimed is:

1. A compound of Formula I:

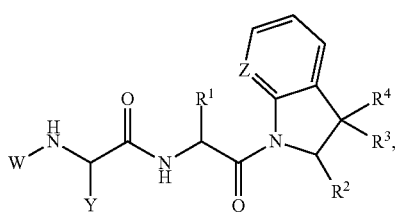

I wherein:

W is selected from the group a) H, b) $C_{1-6}$-alkyl that optionally includes 1-3 deuterium atoms, c) $C_{1-6}$-alkyl that optionally may be substituted with $SO_2R^5$ and $OR^5$ Y is $C_{1-6}$-alkyl that optionally may be substituted with $OR^5$;

Z is N;

$R^1$ is selected from the group a) $C_{1-6}$-alkyl that optionally may be substituted with $SO_2R^5$, b) $C_{3-7}$-cycloalkyl, c) heterocyclic, and d) aryl;

$R^2$ is $C_{1-6}$-alkyl that optionally may be substituted with $NHC(O)R^6$, $NHSO_2R^5$, $NHCOOR^6$ and $NHR^6$;

$R^3$ and $R^4$ may be the same or different and each is independently selected from the group a) H, and b) $C_{1-6}$-alkyl;

$R^5$ is selected from the group a) H, b) $C_{1-6}$-alkyl, c) $NR^7R^8$, and d) aryl;

$R^6$ is selected from the group a) H b) aryl that optionally may be substituted with $C_{1-6}$-alkyl, $OR^5$, halogen, $C(O)OR^5$, $C(O)NR^7R^8$, aryl, heterocyclyl, $C(O)R^9$, $SO_2R^5$, cyano and $CF_3$, c) $C_{1-6}$-alkyl that optionally may be substituted with $CF_3$, $SO_2R^5$ and aryl that optionally may be substituted with $C_{1-6}$-alkyl and halogen, d) $OR^5$, e) $NR^7R^8$, f) heteroaryl that optionally may be substituted with $C_{1-6}$-alkyl, $OR^5$, halogen, aryl and oxo, and g) heterocyclyl;

$R^7$ and $R^8$ may be the same or different and each is independently selected from the group a) H, b) $C_{1-6}$-alkyl, and c) aryl; and $R^9$ is selected from the group a) $C_{1-6}$-alkyl, and b) aryl;

or a pharmaceutically acceptable salt thereof.

2. The compound according to claim 1 wherein W is $C_{1-6}$-alkyl.

3. The compound of claim 2 wherein W is methyl.

4. The compound according to claim 1 wherein Y is $C_{1-6}$-alkyl.

5. The compound according to claim 1 wherein Y is methyl.

6. The compound according to claim 1 wherein $R^1$ is $C_{1-6}$-alkyl, or a pharmaceutically acceptable salt thereof.

7. The compound of claim 6 wherein $R^1$ is propanyl.

8. The compound according to claim 1 wherein $R^2$ is $C_{1-6}$-alkyl that is substituted with $NHC(O)R^6$, or a pharmaceutically acceptable salt thereof.

9. The compound of claim 8 wherein $R^2$ is methyl that is substituted with $NHC(O)R^6$ and $R^6$ is selected from aryl and $C_{1-6}$-alkyl, or a pharmaceutically acceptable salty thereof.

10. The compound according to claim 1 wherein $R^2$ is $C_{1-6}$-alkyl that is substituted with $NHSO_2R^5$, or a pharmaceutically acceptable salt thereof.

11. The compound of claim 10 wherein $R^2$ is methyl that is substituted with $NHSO_2R^5$.

12. The compound of claim 11 wherein $R^5$ is methyl or phenyl.

13. The compound according to claim 1 wherein $R^2$ is $C_{1-6}$-alkyl that is substituted with $NHCOOR^6$, or a pharmaceutically acceptable salt thereof.

14. The compound of claim 13 wherein $R^6$ is benzyl or methyl that optionally may be substituted with phenyl, or a pharmaceutically acceptable salt thereof.

15. The compound according to claim 1 wherein $R^2$ is $C_{1-6}$-alkyl that is substituted with $NHR^6$, or a pharmaceutically acceptable salt thereof.

16. The compound according to claim 15 wherein $R^6$ is aryl, or a pharmaceutically acceptable salt thereof.

17. The compound of claim 16 wherein $R^6$ is phenyl or naphathanelyl, or a pharmaceutically acceptable salt thereof.

18. The compound according to claim 1 wherein $R^3$ and $R^4$ are H, or a pharmaceutically acceptable salt thereof.

19. The compound of claim 9 wherein $R^6$ is phenyl that optionally may be substituted with $C_{1-6}$-alkyl, $OR^5$, halogen, $C(O)OR^5$, $C(O)NR^7R^8$, aryl, heterocyclyl, $C(O)R^9$, $SO_2R^5$, cyano and $CF_3$, or a pharmaceutically acceptable salt thereof.

20. The compound according to claim 1 wherein $R^6$ is $NR^7R^8$, or a pharmaceutically acceptable salt thereof.

21. The compound of claim 20 wherein $R^7$ and $R^8$ are independently selected from H, methyl and phenyl.

22. The compound of claim 1 wherein W, Y and $R^1$ are $C_{1-6}$-alkyl; and $R^2$ is $C_{1-6}$-alkyl substituted by $NHCOR^6$; $R^6$ is selected from a) phenyl, b) $C_{1-6}$-alkyl that optionally may be substituted with phenyl, and c) $NR^7R^8$; and $R^7$ and $R^8$ are each independently selected from H, $C_{1-6}$-alkyl and phenyl; or a pharmaceutically acceptable salt thereof.

23. The compound of claim 1 wherein W, Y and $R^1$ are $C_{1-6}$-alkyl; $R^2$ is $C_{1-6}$-alkyl substituted by $NHSO_2R^5$; and $R^5$ is $C_{1-6}$-alkyl or phenyl; or a pharmaceutically acceptable salt thereof.

24. The compound of claim 23 wherein $R^5$ is methyl or phenyl.

25. The compound of claim 1 wherein W, Y and $R^1$ are $C_{1-6}$-alkyl; $R^2$ is $C_{1-6}$-alkyl substituted by $NHCOOR^6$; and $R^6$ is selected from a) aryl and b) $C_{1-6}$-alkyl that optionally may be substituted with aryl; or a pharmaceutically acceptable salt thereof.

26. The compound of claim 25 wherein $R^6$ is selected from a) methyl that optionally may be substituted with phenyl, and b) phenyl; or a pharmaceutically acceptable salt thereof.

27. The compound of claim 1 wherein W, Y and $R^1$ are $C_{1-6}$-alkyl; $R^2$ is $C_{1-6}$-alkyl substituted by $NHR^6$; and $R^6$ is aryl, or a pharmaceutically acceptable salt thereof.

28. The compound of claim 27 wherein $R^6$ is selected from phenyl and naphthalenyl.

29. The compound of claim 1 selected from:
N—{(S)-1-[(S)-3-Methyl-2-((S)-2-methylamino-propionylamino)-butyryl]-2,3-dihydro-1H-pyrrolo[2,3-b]pyridin-2-ylmethyl}-benzamide hydrochloride;

(S)—N—{(S)-1-[2-(Acetylamino-methyl)-2,3-dihydro-pyrrolo[2,3-b]pyridine-1-carbonyl]-2-methyl-propyl}-2-methylamino-propionamide hydrochloride;

(S)-2-Methylamino-N—((S)-2-methyl-1-{2-[(3-methyl-ureido)-methyl]-2,3-dihydro-pyrrolo[2,3-b]pyridine-1-carbonyl}-propyl)-propionamide hydrochloride;

(S)-2-Methylamino-N— {(S)-2-methyl-1-[(S)-2-(phenylacetylamino-methyl)-2,3-dihydro-pyrrolo[2,3-b]pyridine-1-carbonyl]-propyl}-propionamide hydrochloride;

(S)—N—{(S)-1-[(S)-2-(3,3-Dimethyl-ureidomethyl)-2,3-dihydro-pyrrolo[2,3-b]pyridine-1-carbonyl]-2-methyl-propyl}-2-methylamino-propionamide hydrochloride;

(S)-2-Methylamino-N—((S)-2-methyl-1-{(S)-2-[(3-phenyl-ureido)-methyl]-2,3-dihydro-pyrrolo[2,3-b]pyridine-1-carbonyl}-propyl)-propionamide hydrochloride; and (S)-2-Methylamino-N—((S)-2-methyl-1-{(S)-2-[(2-phenyl-propionylamino)-methyl]-2,3-dihydro-pyrrolo[2,3-b]pyridine-1-carbonyl}-propyl)-propionamide hydrochloride;

or a pharmaceutically acceptable salt of any of the foregoing compounds.

30. The compound of claim 1 selected from:
(S)—N—{(S)-1-[(S)-2-(Methanesulfonylamino-methyl)-2,3-dihydro-pyrrolo[2,3-b]pyridine-1-carbonyl]-2-methyl-propyl}-2-methylamino-propionamide hydrochloride; and (S)—N—{(S)-1-[(S)-2-(Benzenesulfonylamino-methyl)-2,3-dihydro-pyrrolo[2,3-b]pyridine-1-carbonyl]-2-methyl-propyl}-2-methylamino-propionamide hydrochloride; or a pharmaceutically acceptable salt of any of the foregoing compounds.

31. The compound of claim 1 selected from:
{(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid methyl ester hydrochloride;

{(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid methyl ester hydrochloride; and {(S)-1-[(S)-3-Methyl-2-((S)-2-methylamino-propionylamino)-butyryl]-2,3-dihydro-1H-pyrrolo[2,3-b]pyridin-2-ylmethyl}-carbamic acid phenyl ester hydrochloride;

or a pharmaceutically acceptable salt of any of the foregoing compounds.

32. The compound of claim 1 selected from:
(S)-2-Methylamino-N—[(S)-2-methyl-1-((S)-2-phenylaminomethyl-2,3-dihydro-pyrrolo[2,3-b]pyridine-1-carbonyl)-propyl]-propionamide hydrochloride; and (S)-2-Methylamino-N—{(S)-2-methyl-1-[(S)-2-(naphthalen-2-ylaminomethyl)-2,3-dihydro-pyrrolo[2,3-b]pyridine-1-carbonyl]-propyl}-propionamide hydrochloride;

or a pharmaceutically acceptable salt of any of the foregoing compounds.

33. A pharmaceutical composition, comprising a therapeutically effective amount of a compound according to claim 1, or a pharmaceutically acceptable salt thereof, as an active ingredient together with a pharmaceutically acceptable carrier or excipient.

* * * * *